United States Patent
Hubbell et al.

(10) Patent No.: US 6,920,780 B2
(45) Date of Patent: Jul. 26, 2005

(54) TENSIOMETER, DRIVE PROBE FOR USE WITH ENVIRONMENTAL TESTING EQUIPMENT, AND METHODS OF INSERTING ENVIRONMENTAL TESTING EQUIPMENT INTO A SAMPLE

(75) Inventors: Joel M. Hubbell, Idaho Falls, ID (US); James B. Sisson, Idaho Falls, ID (US)

(73) Assignee: Bechtel BWXT Idaho, LLC, Idaho Falls, ID (US)

( * ) Notice: Subject to any disclaimer, the term of this patent is extended or adjusted under 35 U.S.C. 154(b) by 146 days.

(21) Appl. No.: 10/376,153

(22) Filed: Feb. 28, 2003

(65) Prior Publication Data

US 2004/0168525 A1 Sep. 2, 2004

(51) Int. Cl.7 .................................................. G01N 1/00
(52) U.S. Cl. .......................................................... 73/73
(58) Field of Search ................................. 73/73, 152.54, 73/152.35, 152.01, 864.74; 175/50, 58–60

(56) References Cited

U.S. PATENT DOCUMENTS

| | | | | |
|---|---|---|---|---|
| 3,898,872 A | * | 8/1975 | Skaling et al. ................. 73/73 |
| 4,068,525 A | * | 1/1978 | Skaling ........................... 73/73 |
| 4,759,227 A | * | 7/1988 | Timmons .................. 73/863.23 |
| 5,000,051 A | * | 3/1991 | Bredemeier .............. 73/863.23 |
| 5,035,149 A | * | 7/1991 | Wierenga ................. 73/863.23 |
| 5,168,765 A | * | 12/1992 | Broussard ................ 73/864.74 |
| 5,644,947 A | | 7/1997 | Hubbell et al. |
| 5,758,538 A | | 6/1998 | Hubbell et al. |
| 5,915,476 A | | 6/1999 | Hubbell et al. |

* cited by examiner

Primary Examiner—Robert Raevis
(74) Attorney, Agent, or Firm—Wells, St. John P.S.

(57) ABSTRACT

A method of inserting a tensiometer into a sample, comprises providing a drive probe configured to be engaged by direct push equipment; supporting a porous member from the drive probe; and driving the drive probe into the sample using a cone penetrometer. A tensiometer comprises a drive probe configured to be engaged by direct push equipment or a cone penetrometer; a porous member supported by the drive probe; and a pressure sensor in pressure sensing relation to the porous member.

26 Claims, 7 Drawing Sheets

TENSIOMETER, DRIVE PROBE FOR USE WITH ENVIRONMENTAL TESTING EQUIPMENT, AND METHODS OF INSERTING ENVIRONMENTAL TESTING EQUIPMENT INTO A SAMPLE

GOVERNMENT RIGHTS

This invention was made with Government support under Contract DE-AC07-99ID13727 awarded by the U.S. Department of Energy. The Government has certain rights in the invention.

TECHNICAL FIELD

The invention relates to environmental testing equipment, tensiometers, methods of inserting environmental testing equipment into samples, and methods of manufacturing environmental testing equipment.

BACKGROUND OF THE INVENTION

Cone penetrometer technology (CPT) has been used widely for investigating strength properties in foundations and road subgrades for over 40 years, and for environmental purposes for the past five years. Prior art uses of cone penetrometer technology for environmental purposes have generally been limited to soil, soil gas, and ground water sampling.

Tensiometers are known in the art and are described, for example in the following U.S. patents which are incorporated herein by reference: U.S. Pat. No. 5,915,476 to Hubbell et al.; U.S. Pat. No. 5,758,538 to Hubbell et al.; and U.S. Pat. No. 5,644,947 to Hubbell et al. A conventional tensiometer includes a sealed tube defining a chamber which is normally completely filled with water, a hollow porous tip on one end of the tube, and a vacuum gauge connected to the water chamber. The porous tip is inserted in the soil and establishes liquid contact between the water in the tube and the moisture in the soil surrounding the tip. Relatively dry soil tends to pull water from the tube through the porous tip. However, because the tube is sealed, only a minute amount of water is actually withdrawn. Therefore, the water in the tube is placed under tension by the pulling effect of the dry soil, thus creating a measurable subatmospheric pressure in the tube. Higher moisture contents in the soil produce correspondingly less vacuum in the tube. Completely saturated soils register substantially zero vacuum or atmospheric pressure.

U.S. Pat. No. 5,915,476 to Hubbell and Sisson discloses an advanced tensiometer included in a monitoring well comprising a conduit defining a passageway, the conduit having a proximal end, an opposite distal end, and a given inside diametral dimension; a coupler connected in fluid flowing relationship with the passageway; a geophysical monitoring device dimensioned for slidable movement in the passageway which is defined by the conduit, and wherein the geophysical monitoring device has a connector for releasable mating cooperation with the coupler; and a porous housing borne by the coupler and connected in fluid flowing relation relative thereto.

Conventional techniques for installing tensiometers require drilling wells with hand augers (if shallow), hollow stem augers, or rotary drill rigs, resulting in drill cuttings being brought to the surface. The drill cuttings thus produced then have to be disposed.

Some monitoring sites have stringent requirements for drilling. In some sites, such as contaminated sites, it is undesirable to have drill cuttings removed to land surface or to have large diameter boreholes drilled. Therefore, it would be desirable to provide tensiometers that can be inserted into samples without the need for drilling.

BRIEF DESCRIPTION OF THE DRAWINGS

Preferred embodiments of the invention are described below with reference to the following accompanying drawings.

FIG. 1 is a front elevational view, in cross-section, of a drive probe embodying various aspects of the invention. FIG. 1 also shows a cross-sectional view of a porous member supported by the drive probe.

FIG. 7 is a front elevational view, in cross-section, of a drive probe including a reduced diameter end, in accordance with an alternative embodiment of the invention. FIG. 7 also shows a cross-sectional view of a porous member supported by the drive probe.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

The invention provides a tensiometer comprising a drive probe configured to be engaged by a drive rod or inner drive tube of direct push equipment; a porous member supported by the drive probe; and a pressure sensor in pressure sensing relation to the porous member.

Another aspect of the invention provides a tensiometer comprising a drive probe including a tip portion, and a hollow elongated portion extending from the tip portion and having an inner surface, an outer surface, and apertures extending between the inner surface and outer surface, the drive probe further including an inner tapered surface in fluid communication with the inner surface of the hollow elongated portion, the tapered surface having a first diameter proximal the tip portion and a second diameter, greater than the first diameter, distal from the tip portion, the tapered surface being configured to be selectively engaged by a drive rod of direct push equipment; a porous member supported by the hollow elongated portion of the drive probe; and a pressure sensor in pressure sensing relation to the porous member.

Another aspect of the invention provides a tensiometer comprising a drive probe including a conical tip portion, and a hollow elongated portion extending from the tip portion and having an inner surface, an outer surface, and apertures extending between the inner surface and outer surface, the drive probe further including an inner tapered surface in fluid communication with the inner surface of the hollow elongated portion, the tapered surface having a first diameter proximal the tip portion and a second diameter, greater than the first diameter, distal from the tip portion, the tapered surface being configured to be selectively engaged by a drive rod of direct push equipment, the drive probe further including an end opposite the tip portion, the end including an inner surface having an inner diameter greater than the second diameter and having inner threads configured to mate with outer threads of an outer guide pipe of direct push equipment; a porous member supported by the hollow elongated portion of the drive probe; and a pressure sensor in pressure sensing relation to the porous member.

Another aspect of the invention provides a drive probe for use with environmental testing equipment, comprising a conical tip portion; and a hollow elongated portion extending from the tip portion and having an inner surface, an outer surface, and apertures extending between the inner surface and outer surface, the drive probe further including an inner tapered surface in fluid communication with the inner surface of the hollow elongated portion, the tapered surface having a first diameter proximal the tip portion and a second diameter, greater than the first diameter, distal from the tip portion, the tapered surface being configured to be selectively engaged by a drive rod of direct push equipment, the drive probe further including an end opposite the tip portion, the end including an inner surface having an inner diameter greater than the second diameter and having inner threads configured to mate with outer threads of an outer guide pipe of direct push equipment.

Another aspect of the invention provides a method of inserting a tensiometer into a sample, comprising providing a drive probe configured to be engaged by a drive rod of direct push equipment; supporting a porous member from the drive probe; and driving the drive probe into the sample using direct push equipment.

Another aspect of the invention provides a method of manufacturing a tensiometer, the method comprising configuring a drive probe configured to be engaged by a drive rod of direct push equipment; supporting a porous member from the drive probe; and supporting a pressure sensor in the drive probe, in pressure sensing relation to the porous member.

One aspect of the invention provides a tool defined by modification of a direct push instrument, and a process to install the tool.

One aspect of the invention provides modifying a cone penetrometer drive probe to incorporate a tensiometer. The drive probe can be driven to the depth of interest and the tensiometer gasket/transducer/guide pipe installed to obtain soil water potential measurements in a few minutes to an hour's time. This installation can be used to obtain a short-term, single measurement, or can be left in place for long term measurements. The tensiometer can be serviced and the transducer calibrated or replaced, as required. Because the gasket/transducer/guide pipe is installed following driving the cone penetrometer, there are no stresses applied to the transducer. The tensiometer can be used to obtain multiple measurements with depth in a single well (if, for each measurement, driving is stopped and a measurement is taken before the probe is driven to the next depth).

One aspect of the invention provides a modification of direct push technology (of the type used with cone penetrometers) to allow tensiometeric (soil water potential) measurements in situ. One aspect of the invention provides a combination of a tensiometer according to one of the above incorporated patents with direct push technology. Another aspect of the invention allows installation of a tensiometer without the need to drill a well and bring drill cuttings to land surface.

Figure 1:
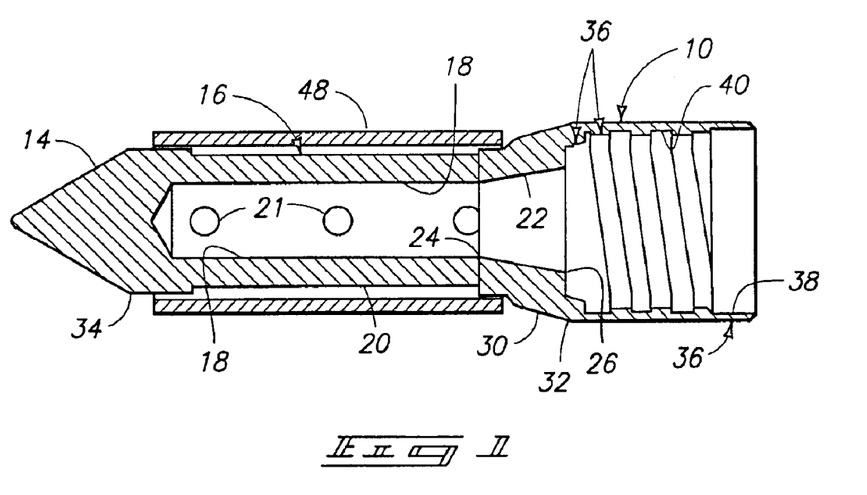

FIG. 1 shows a drive probe 10 embodying various aspects of the invention. In the illustrated embodiment, the drive probe 10 is configured to be engaged by a drive rod (inner drive tube) of direct push equipment 12 such as a direct push machine, device, or rig of the type used with cone penetrometers (see FIG. 5). Other pushing techniques can also be used. The drive probe 10 is formed of, comprises, or consists essentially of metal, such as stainless steel.

The drive probe 10 includes a tip portion 14. The tip portion 14 is conical in the illustrated embodiment. The drive probe 10 further includes a hollow elongated portion 16 extending from the tip portion 14. The hollow elongated portion 16 has an inner surface 18, an outer surface 20, and one or more apertures 21 extending between the inner surface 18 and outer surface 20. In the illustrated embodiment, the inner surface 18 is cylindrical and the outer surface 20 is cylindrical.

The drive probe 10 further includes an inner tapered surface 22 in fluid communication with the inner surface 18 of the hollow elongated portion 16. The inner tapered surface 22 has a first end including a first diameter 24 proximal the tip portion 14. The inner tapered surface 22 further has a second end having a second diameter 26, greater than the first diameter 24, distal from the tip portion 14. The tapered surface 22 is selectively engaged by a drive rod 28 of the direct push equipment or cone penetrometer type rig 12 (see FIG. 5). The drive probe 10 further includes an exterior frustroconical or generally frustroconical surface 30, outside of the portion of the drive probe 10 that has the inner tapered surface 22.

Figure 5:
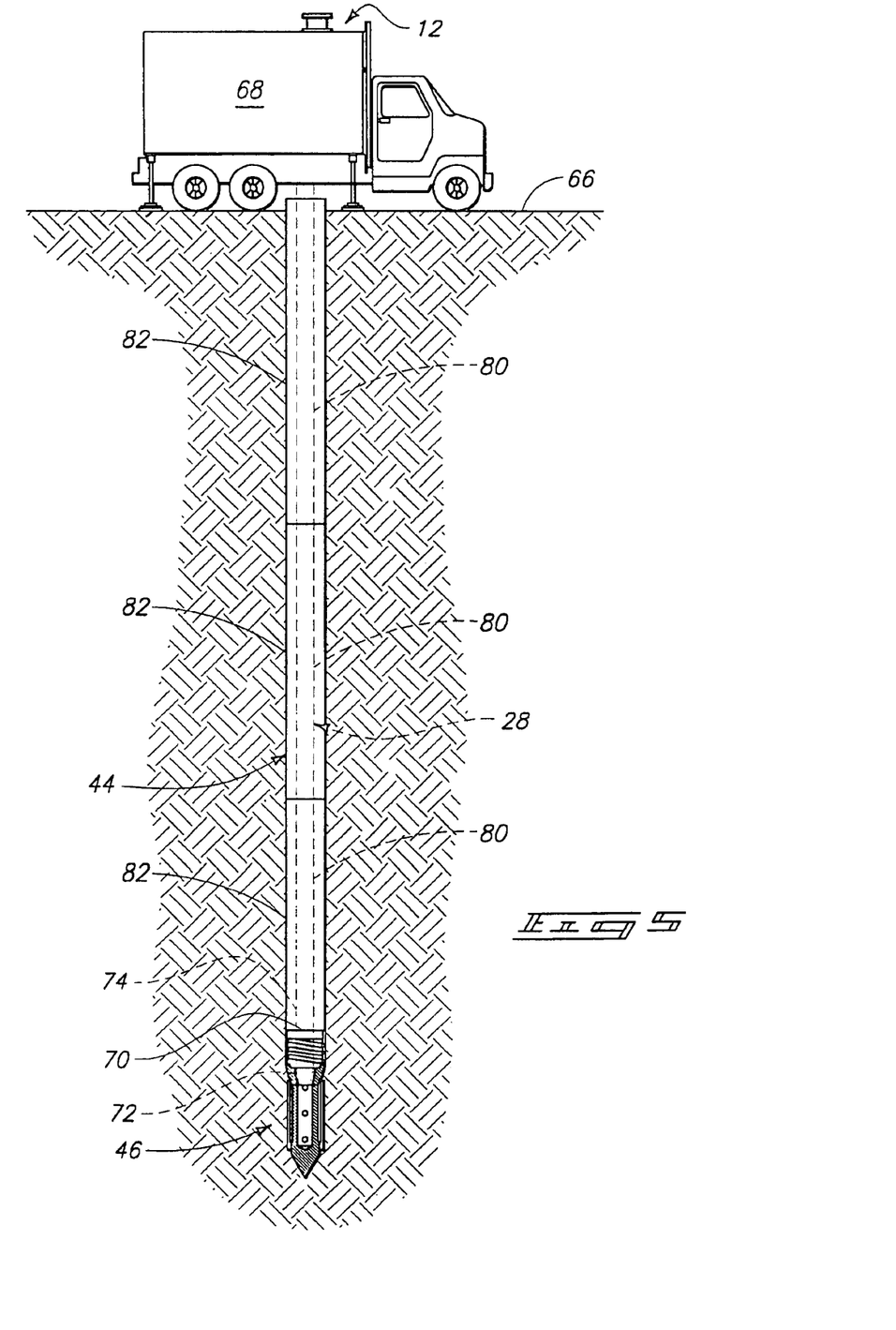
FIG. 5 is a front elevational view illustrating installation of the drive probe of FIG. 1 into a sample.

The drive probe 10 further includes an end portion 36 opposite the tip portion 14. More particularly, the tapered surface 22 is located between the end portion 36 and the tip portion 14. The end portion 36 includes an inner surface 38 having an inner diameter greater than the maximum diameter 26 of the tapered portion. The inner surface 38 has inner threads 40 configured to mate with outer threads 42 of an outer guide pipe 44 (FIG. 2) of direct push equipment 12 (FIG. 5).

In the embodiment shown in FIG. 1, the surface 30 has a maximum diameter 32 greater than the maximum diameter 34 of the conical tip portion 14, which aids in insertion of the drive probe 10. More particularly, in the embodiment shown in FIG. 1, the drive probe 10 generally has two outer diameters. This is believed to provide better contact with the soil. In one alternative embodiment, a single diameter version is provided having an outer diameter that is the same as the diameter of an outer guide pipe 44. In this embodiment, the outer guide pipe 44 is used as a driving pipe, and inner threads 40 are sized to engage outer threads of an outer guide pipe. For example, the frustroconical surface 30 can be omitted and the outer surface 20 can have the same outer diameter as the end 36.

Figure 2:
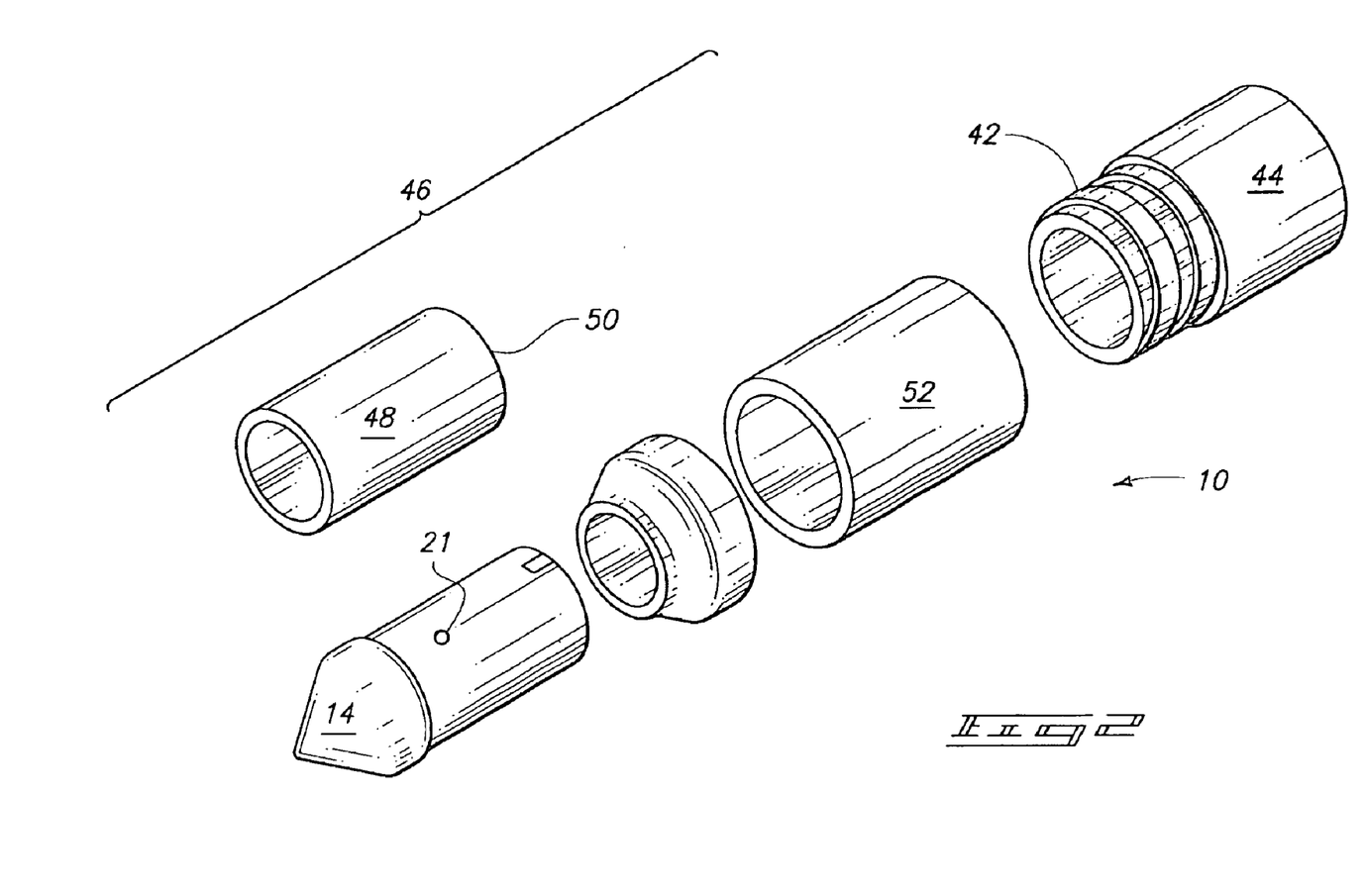
FIG. 2 is an exploded perspective view of components used to manufacture the drive probe of FIG. 1, in one embodiment.
Figure 3:
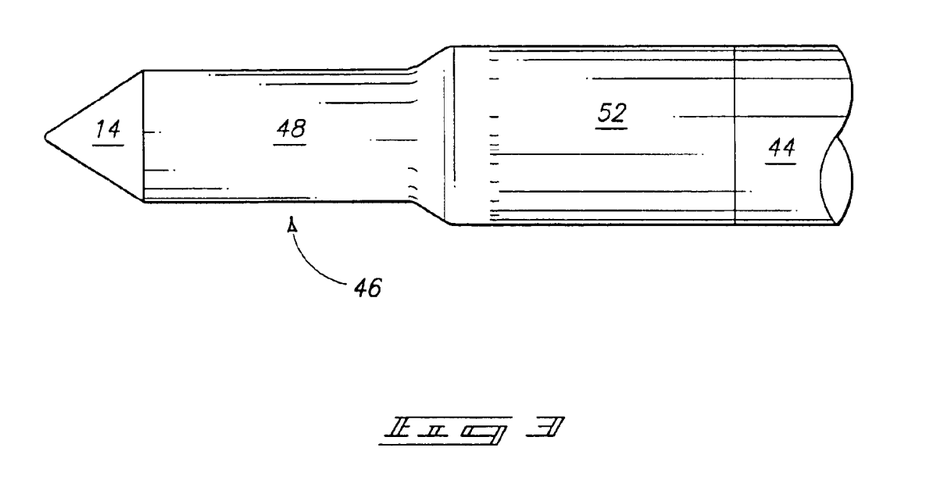
FIG. 3 is a perspective view showing assembly of the components of FIG. 2 as well as an outer guide pipe.

The drive probe 10 of FIG. 1 can be used to define various environmental (e.g., geophysical or hydrogeological) testing devices. FIGS. 2 and 3 show a tensiometer 46 including the drive probe 10 of FIG. 1. FIG. 2 is an exploded view and FIG. 3 shows components of FIG. 2 after assembly. The tensiometer 46 further includes a porous member 48 supported by the drive probe 10. More particularly, in the illustrated embodiment, the porous member 48 includes the general shape of a hollow cylinder and has an inner cylindrical surface 50 selectively supported on or about the outer cylindrical surface 20 of the hollow elongated portion 16 of the drive probe 10 (FIG. 1). In the illustrated embodiment, the porous member 48 is a porous stainless steel membrane. In one embodiment, during manufacture, the cylindrical porous stainless steel membrane 48 is slid over the conical tip portion 14 to surround the hollow elongated portion 16, and the porous membrane is welded in place over the hollow elongated portion 16 (e.g., is welded to the hollow elongated portion 16, to the tip portion 14, or to or proximate the surface 30. In one embodiment, the porous stainless steel membrane 48 is a SW-070P 2×⅛ stainless steel filter available from Soil Measurement Systems.

During manufacture, in one embodiment, the conical tip portion 14 and hollow elongated portion 16 extending from the tip portion 14 are machined as a unitary, integral piece, and an adapter portion 52 is welded to the hollow elongated portion 16. The adapter portion 52, in one embodiment, is manufactured of two pieces, a first piece that defines the inner tapered surface 22 and the surface 30, and a second, cylindrical, piece that defines the end portion 36 having the inner threads 40 (FIG. 1) configured to mate with outer guide pipe 44. The second piece of the adapter portion 52 has a diameter and threads appropriate for mating with a commercially available outer guide pipe. Different adapters can be used for different outer guide pipe designs. In an alternative embodiment, the adapter 52 is a unitary piece. In an alternative embodiment, the entire drive probe 10 is unitary or one-piece. In another alternative embodiment, the tip portion 14 is separate from and attachable to the hollow elongated portion 16 (e.g., by threads or by welding). In this alternative embodiment, the tip portion 14 can be added after the porous member 48 is slid over the hollow elongated portion 16 and can, for example, hold the porous member 48 in place.

Figure 4:
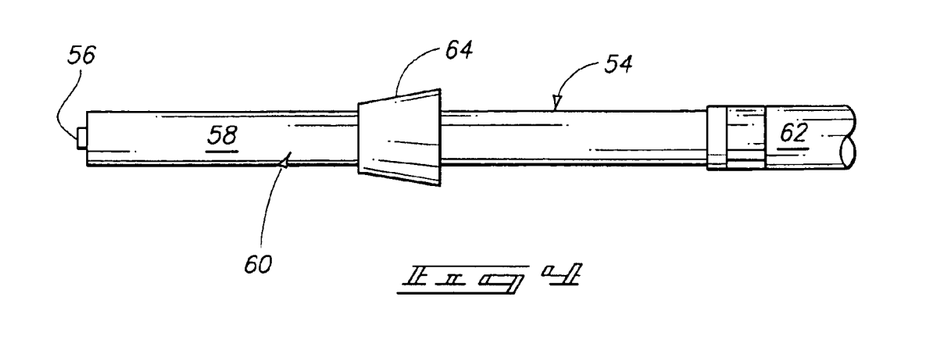
FIG. 4 is a perspective view of a pressure transducer assembly that is inserted at least part way into the components of FIG. 2, via the outer guide pipe shown in FIG. 3.

The tensiometer 46 further includes a pressure sensor (see FIG. 4) in pressure sensing relation to the porous member 48. The pressure sensor is defined by a pressure transducer assembly 54 including a transducer 56 configured to be supported in the inner surface 18 of the hollow elongated portion 16 (FIG. 1). The assembly 54 further includes a conduit 58 supporting the transducer and passing leads from the transducer to land surface. In one embodiment, the conduit 58 includes two portions—a generally rigid portion 60 supporting the transducer, and an elongated, possibly flexible portion 62 extending from the portion 60. The assembly 54 further includes a seal member 64 supported by the conduit 58 (e.g., supported by the portion 60) and configured to engage the inner tapered surface 22 after the drive rod is removed. In the illustrated embodiment, the seal member 64 is a stopper or frustroconical seal member with an internal aperture along its major axis for sliding engagement over the conduit 58. Other types and shapes of seals or sealing mechanisms could be employed, such as o-rings, to form a seal at this location. The seal member 64 is made of plastic, rubber or other suitable natural or synthetic resilient material. In one embodiment, at least a portion 60 of the conduit is generally rigid and is manufactured, for example, of metal. The metal can be stainless steel, copper, or any other desired material.

FIG. 5 shows the tensiometer 46 being installed in a sample using direct push equipment or a cone penetrometer type rig 12. The inner drive rod 28 engages the tapered surface 22 and is used to push the tensiometer 46 into a sample 66 (e.g., into the ground). The direct push equipment 12 includes, for example, an impact hammer (not shown) supported from a rig 68 (e.g., a truck or construction vehicle) that engages the inner drive rod 28 and pushes the drive rod 28, thus pushing the tensiometer 46. In the illustrated embodiment, the inner drive rod 28 has a lower end that includes a tapered surface 72 sized to engage the internal tapered surface 22. The inventors have recognized that tapering the lower end 70 of the inner drive rod 28 helps the inner drive rod 28 push the tensiometer 46 along a relatively straight path. The inner drive rod 28 typically is defined by multiple sections. Other than the lower end 70 of the lowermost inner drive rod section 74, each end of a section 80 has threads (not shown) configured to mate with complementary threads (not shown) of another section. As the tensiometer 46 is pushed into the sample 66, additional guide rod sections 80 are added, in one embodiment.

In the illustrated embodiment, the outer guide pipe 44 has threads 42 configured to mate with the inner threads 40 of the end portion 36, as described above. In the illustrated embodiment, the outer guide pipe 44 is pulled by the tensiometer 46 while the tensiometer 46 is pushed by the inner drive rod 28. In the illustrated embodiment, the drive probe 10 is sized to be used with a conventional outer guide pipe 44 of the direct push equipment 12. Such guide pipes 44 often have unique thread designs. Different embodiments of the drive probe 10 have different thread designs and inner diameters appropriate for engaging a variety of different conventional guide pipe threads.

The outer guide pipe 44 typically is defined by multiple sections 84. Each end of a section 84 has threads 42 configured to mate with complementary threads of another section (or with the end portion 36). As the tensiometer 46 is pushed into the sample, and additional inner drive rod sections 80 are added, additional outer guide pipe sections 82 are also added, in one embodiment.

After insertion of the tensiometer 46, the inner drive rod 28 is removed and the pressure transducer assembly 54 is inserted. The outer guide pipe 44 remains. In one embodiment, in addition to or instead of the pressure transducer assembly 54, a geophysical instrument or data gathering device is inserted into the guide pipe 44 after the inner drive rod 28 is removed. The outer guide pipe 44 can be metal, such as steel or stainless steel. The outer guide pipe 44 can also be or consist essentially of opaque plastic. However, in the illustrated embodiment, the outer guide pipe 44 is or consists essentially of clear or transparent plastic. The outer guide pipe 44 can also include portions or windows of clear plastic or can be or consist of translucent plastic in alternative embodiments.

In one embodiment (see FIG. 6), after the inner drive rod 28 is removed, a data capture device 84 is inserted into the clear plastic guide pipe 44 and portions or all of the sample, down to the lower end of the guide pipe, are viewed or recorded (e.g., using a data recording device 85 coupled to the data capture device 84). In the illustrated embodiment, the data capture device 84 is a camera, such as a video camera. In the illustrated embodiment, the data capture device 84 is rotatable (e.g., 360 degrees) about the axis defined by the length of the guide pipe 44.

Figure 7:
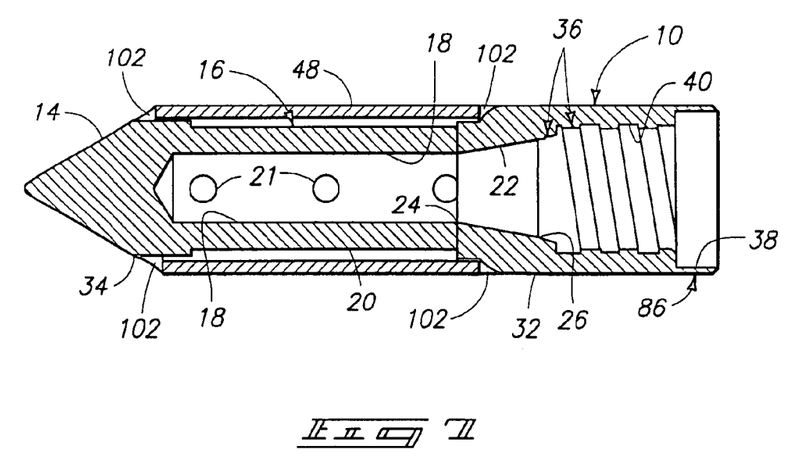

In one alternative embodiment, shown in FIG. 7, an end portion 86 has a diameter smaller than the diameter of the end portion 36 of FIG. 1. The end portion 86 is configured to be engaged by a drive rod or hollow drive tube of direct push equipment. More particularly, this alternative embodiment is substantially similar to the embodiment shown in FIG. 1, like reference numerals indicating like components, except that the end portion 86 has a smaller outer diameter and inner diameter than the embodiment of FIG. 1 and the end portion 86 includes internal threads sized to be engaged by outer threads of a drive rod or hollow drive tube. Welds 102 secure the porous member 48 to the elongated portion 16 and shoulder 132 of the end 86.

Figure 6:
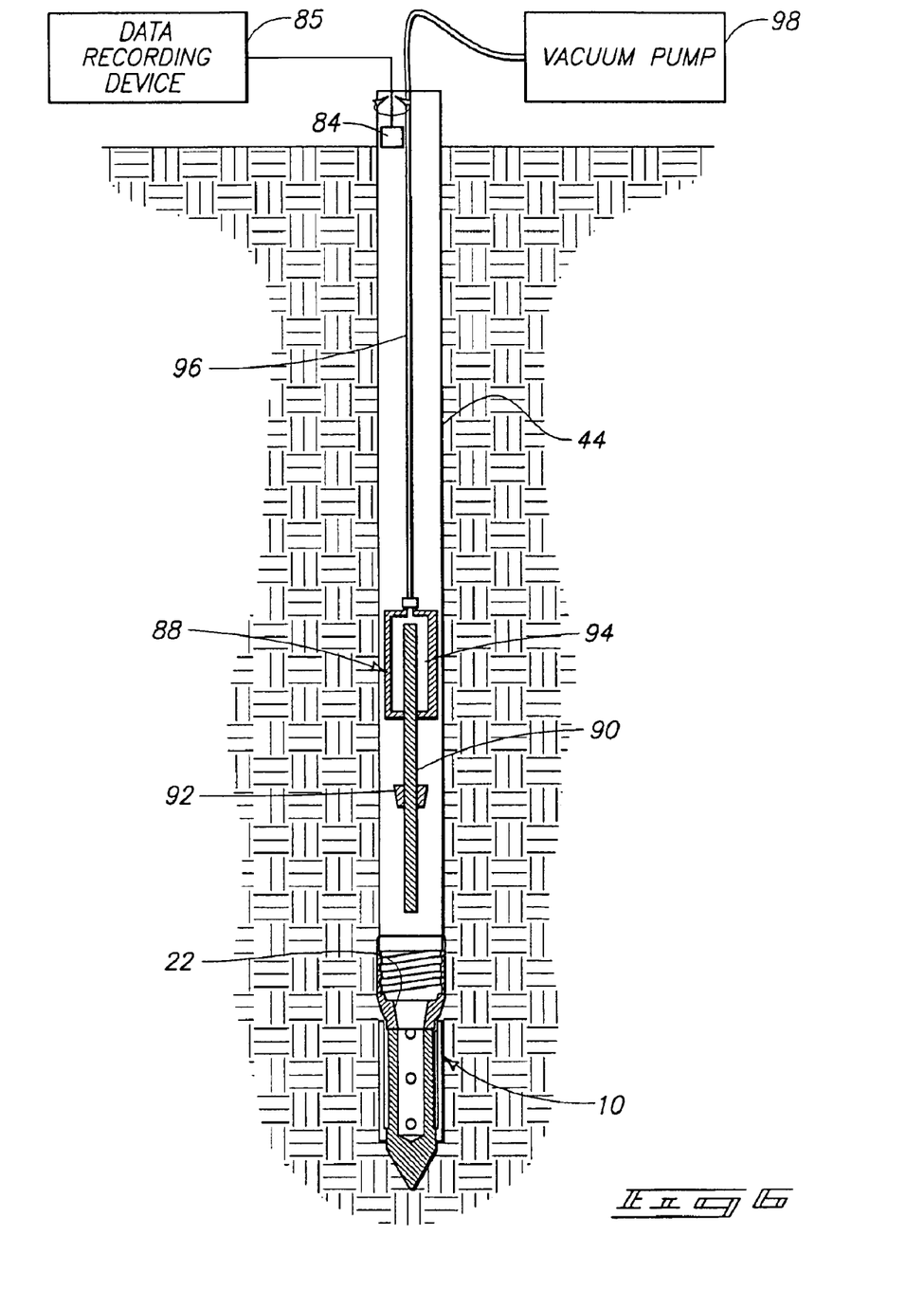
FIG. 6 is a front elevational schematic view illustrating use of a sampling device, in accordance with an alternative embodiment of the invention, with the drive probe of FIG. 1.

In another embodiment shown in FIG. 6, the drive probe 10 can be used to define a suction lysimeter 88 instead of a tensiometer 46. The difference is in the device added in the interior of the outer guide pipe 44 after installation and after the inner drive rod 28 has been removed. A lysimeter 88 could be used that includes, for example, a tube that is inserted into the drive probe 10, and a stopper 92 surrounding the tube 90 that selectively engages the inner tapered surface 22. The tube 90 leads to a chamber 94 that is in fluid communication with a separate tube or line 96 leading to land surface. The tube 96 is also used to raise and lower the chamber 94, tube 90, and stopper 92. In the illustrated embodiment, a tube is used, and the tube 96 is shown as being fluidly coupled to a vacuum pump 98. In one embodiment, lysimeter components such as are described in U.S. Pat. No. 5,915,476 (incorporated herein by reference) are used.

Figure 8B:
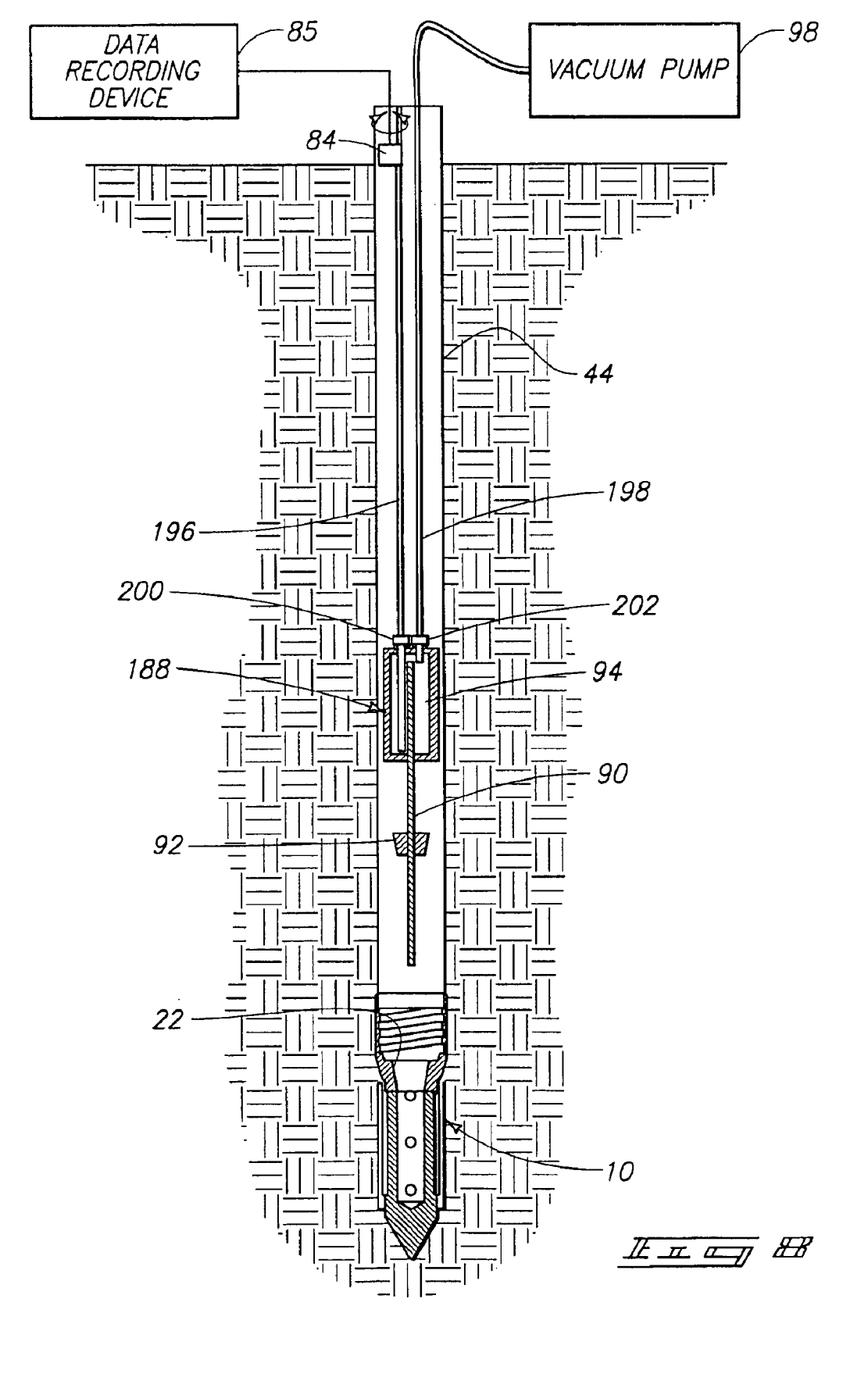
FIG. 8 is a front elevational schematic view illustrating use of a sampling device, in accordance with an alternative embodiment of the invention, with the drive probe of FIG. 1.

While FIG. 6 shows a single tube suction lysimeter 88, FIG. 8 shows a dual tube suction lysimeter 188. A tube 196 is included for use as a sample tube, and a tube 198 is included as a pressure tube. This version can be used to withdraw samples for sampling without removing the lysimeter to land surface. This version allows sampling at greater depths. The tubes 196 and 198 are connected using, for example, Swagelok connectors 200 and 202 (available from Swagelok Company, 29500 Solon Road, Solon, Ohio 44139) to male pipeweld connectors (not shown) on the lysimeter 188.

A tight seal between the seal 92 and surface 22 is achieved, in one embodiment, by weighting the lysimeter 88 or 188. Alternatively, external thread can be provided on the lysimter 88 or 188 (e.g., near the top of the lysimeter) for engagement by a guide tube, e.g., the outer guide pipe 44, which holds down the lysimeter, which can be used to raise and lower the lysimeter, and which also provides a passage for the tube 96 or tubes 196 and 198.

Other geophysical instruments can be lowered inside the outer guide pipe 44 as desired, whether the drive probe 10 is used to define a tensiometer, lysimeter, or neither.

In operation, the drive probe 10 is driven until the porous member 48 is located at the depth of interest. The inner drive rod 28 is then unscrewed at land surface and an inner flexible hose or guide pipe 62 supporting gasket or seal 64 and transducer 56 is placed inside the outer guide pipe or casing 44 to connect with the adaptor 52. This makes the cone penetrometer into an advanced tensiometer having the advantages of the tensiometer described in U.S. Pat. No. 5,915,476 to Hubbell et al. (incorporated herein by reference) that can be monitored from land surface.

Thus, a drive probe has been provided that is valuable for installing tensiometers at sites with contamination without having to bring materials to land surface, thereby saving considerable time and money. The drive probe with the porous membrane adapted to be used with a direct push machine can be removed at a later time if so desired and reused at other sites. A method has been provided that can be used at contaminated sites where a sacrificial drive rod is a lower cost alternative to disposal of potentially contaminated earthen materials. Complete removal of the monitoring equipment is possible at a later time, if required. The invention allows monitoring at sites that could not previously be monitored because of the waste disposal problems.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

What is claimed is:

1. A tensiometer comprising:
   a drive probe configured to be engaged by a drive rod of direct push equipment, the drive probe having an end portion having internal threads configured to be engaged by outer threads of a hollow outer guide pipe, the drive probe further including a tip portion, a hollow elongated portion extending portion extending from the tip portion and having an inner surface, a cylindrical outer surface, and apertures extending between the inner surface and outer surface;
   a porous member has an inner cylindrical surface supported by the outer surface of the elongated portion of the drive probe; and
   a pressure sensor in pressure sensing relation to the porous member.

2. A tensiometer in accordance with claim 1 wherein the drive probe is configured to be engaged by a drive rod of direct push equipment.

3. A tensiometer in accordance with claim 1 wherein the drive probe further includes an inner tapered surface in fluid communication with the inner surface of the hollow elongated portion, the tapered surface having a first diameter proximal the tip portion and a second diameter, greater than the first diameter, distal from the tip portion, the tapered surface being configured to be selectively engaged by a drive rod of direct push equipment.

4. A tensiometer in accordance with claim 3 wherein the tapered surface is configured to be selectively engaged by a drive rod of a type used with a cone penetrometer.

5. A tensiometer in accordance with claim 4 wherein the porous member comprises metal.

6. A tensiometer in accordance with claim 4 wherein the porous member consists essentially of stainless steel.

7. A tensiometer in accordance with claim 3 wherein the pressure sensor is defined by a pressure transducer assembly including a transducer configured to be supported in the inner surface of the hollow elongated portion, a conduit supporting the transducer, and a seal member supported by the conduit and configured to engage the inner tapered surface after the drive rod is removed.

8. A tensiometer in accordance with claim 3 wherein the drive probe further includes an end portion opposite the tip portion, the end portion including an inner surface having an inner diameter greater than the second diameter and having inner threads configured to mate with outer threads of an outer guide pipe of direct push equipment.

9. A tensiometer in accordance with claim 8 and further comprising an outer guide pipe having threads configured to mate with the inner threads of the end portion opposite the tip portion.

10. A tensiometer in accordance with claim 9 and further comprising a geophysical instrument in the guide pipe.

11. A tensiometer in accordance with claim 9 wherein the outer guide pipe is metal.

12. A tensiometer in accordance with claim 9 wherein the outer guide pipe consists essentially of clear plastic.

13. A tensiometer in accordance with claim 9 wherein the outer guide pipe consists essentially of opaque plastic.

14. A tensiometer in accordance with claim 8 wherein the drive probe comprises metal.

15. A tensiometer in accordance with claim 8 wherein the drive probe consists essentially of stainless steel.

16. A drive probe for use with environmental testing equipment, comprising:

a conical tip portion; and a hollow elongated portion extending from the tip portion and having an inner surface, an outer surface, and apertures extending between the inner surface and outer surface, the drive probe further including an inner tapered surface in fluid communication with the inner surface of the hollow elongated portion, the tapered surface having a first diameter proximal the tip portion and a second diameter, greater than the first diameter, distal from the tip portion, the tapered surface being configured to be selectively engaged by a drive rod of direct push equipment, the drive probe further including an end portion opposite the tip portion, the end portion including an inner surface having an inner diameter greater than the second diameter and having inner threads configured to mate with outer threads of an outer guide pipe of direct push equipment.

17. A drive probe in accordance with claim 16 wherein the tapered surface is configured to be selectively engaged by a drive rod configured for use with a cone penetrometer.

18. A method of inserting a tensiometer into a sample, comprising:

providing a drive probe configured to be engaged by a drive rod of direct push equipment;

supporting a porous member from the drive probe; and driving the drive probe into the sample using a drive rod of direct push equipment, and wherein the drive probe includes an internal tapered surface configured to engage the drive rod, the method further comprising tapering an end of the drive rod to define a taper corresponding to the internal tapered surface, for engagement of the tapered end of the drive rod with the internal tapered surface.

19. A method of inserting a tensiometer into a sample in accordance with claim 18 wherein supporting a porous member from the drive probe comprises welding a generally cylindrical porous member to the drive probe.

20. A method of inserting a tensiometer into a sample in accordance with claim 18 and further comprising using the drive probe as a suction lysimeter.

21. A method of inserting a tensiometer into a sample in accordance with claim 18 wherein providing a drive probe comprises defining a drive probe including a tip portion, and a hollow elongated portion extending from the tip portion and having an inner surface, an outer surface, and apertures extending between the inner surface and outer surface, the drive probe further including an inner tapered surface in fluid communication with the inner surface of the hollow elongated portion, the tapered surface having a first diameter proximal the tip portion and a second diameter, greater than the first diameter, distal from the tip portion, the method further comprising engaging the tapered surface with a drive rod of direct push equipment to push the drive probe into the sample.

22. A method of inserting a tensiometer into a sample in accordance with claim 21 and further comprising a pressure sensor defined by a pressure transducer configured to be supported inside the inner surface of the hollow elongated portion, providing a conduit, supporting the transducer from the conduit, and supporting a seal member from the conduit, and causing the seal member to engage the inner tapered surface, after the drive rod is removed, with the transducer located beyond the inner tapered surface in the direction of the tip.

23. A method of inserting a tensiometer into a sample in accordance with claim 18 wherein providing a drive probe comprises defining a drive probe including a conical tip portion, and a hollow elongated portion extending from the tip portion and having an inner surface, and an outer surface, defining apertures between the inner surface and outer surface, defining an inner tapered surface in the drive probe, in fluid communication with the inner surface of the hollow elongated portion, with a first diameter proximal the tip portion and a second diameter, greater than the first diameter, distal from the tip portion, the inner tapered surface being configured to be selectively engaged by a drive rod of direct push equipment, and defining an end portion opposite the tip portion, the end portion including an inner surface having an inner diameter greater than the second diameter and having inner threads configured to mate with outer threads of an outer guide pipe of direct push equipment, the inner tapered surface being located between the end portion and the tip portion.

24. A method of inserting a tensiometer into a sample in accordance with claim 23 and further comprising providing an outer guide pipe having threads configured to mate with the inner threads of the end portion opposite the tip portion and mating the outer guide pipe with the inner threads of the end portion.

25. A method of inserting a tensiometer into a sample in accordance with claim 24 and further comprising inserting a geophysical instrument into the outer guide pipe.

26. A method of inserting a tensiometer into a sample in accordance with claim 18 wherein providing a drive probe comprises:

defining a conical tip portion and a hollow elongated portion extending from the tip portion, the hollow elongated portion having an inner surface, an outer surface, and apertures extending between the inner surface and outer surface; and welding an adapter portion to the hollow elongated portion, the adapter portion defining an inner tapered surface in fluid communication with the inner surface of the hollow elongated portion, the tapered surface having a first diameter proximal the tip portion and a second diameter, greater than the first diameter, distal from the tip portion, the tapered surface being configured to be selectively engaged by a drive rod of direct push equipment, the adapter portion further including an end portion opposite the tip portion, the end portion including an inner surface having an inner diameter greater than the second diameter and having inner threads configured to mate with outer threads of an outer guide pipe of direct push equipment.

* * * * *